(12) United States Patent
Reynolds et al.

(10) Patent No.: US 8,142,488 B2
(45) Date of Patent: Mar. 27, 2012

(54) STENT REMOVAL AND REPOSITIONING AID AND ASSOCIATED METHOD

(75) Inventors: Jason M. Reynolds, Charlotte, NC (US); Jeff Reuther, Charlotte, NC (US); Eric K. Mangiardi, Charlotte, NC (US)

(73) Assignee: Merit Medical Systems, Inc., South Jordan, UT (US)

( * ) Notice: Subject to any disclaimer, the term of this patent is extended or adjusted under 35 U.S.C. 154(b) by 101 days.

(21) Appl. No.: 11/577,859

(22) PCT Filed: Oct. 25, 2005

(86) PCT No.: PCT/US2005/038519
§ 371 (c)(1),
(2), (4) Date: Dec. 17, 2007

(87) PCT Pub. No.: WO2006/047573
PCT Pub. Date: May 4, 2006

(65) Prior Publication Data
US 2008/0140181 A1    Jun. 12, 2008

(51) Int. Cl.
*A61F 2/06* (2006.01)
(52) U.S. Cl. .................................... 623/1.15; 623/1.11
(58) Field of Classification Search .............. 623/1.15, 623/1.12, 1.16, 1.11, 1.23, 1.13
See application file for complete search history.

(56) References Cited

U.S. PATENT DOCUMENTS

| | | |
|---|---|---|
| 5,035,706 A | 7/1991 | Giantureo et al. |
| 5,156,609 A | 10/1992 | Nakao et al. |
| 5,749,921 A * | 5/1998 | Lenker et al. ............. 623/1.42 |
| 5,776,186 A | 7/1998 | Uflacker |
| 5,897,589 A | 4/1999 | Cottenceau et al. |
| 5,941,895 A | 8/1999 | Myler et al. |
| 6,090,129 A | 7/2000 | Ouchi |
| 6,149,651 A | 11/2000 | Drewry et al. |
| 6,149,681 A * | 11/2000 | Houser et al. ............. 623/1.12 |
| 6,165,209 A | 12/2000 | Patterson et al. |
| 6,187,016 B1 | 2/2001 | Hedges et al. |
| 6,241,757 B1 | 6/2001 | An et al. |
| 6,361,540 B1 | 3/2002 | Gauderer et al. |
| 6,375,676 B1 | 4/2002 | Cox |
| 6,607,539 B1 | 8/2003 | Hayashi et al. |
| 6,676,692 B2 | 1/2004 | Rabkin et al. |

(Continued)

FOREIGN PATENT DOCUMENTS
DE    10118944    10/2002
(Continued)

OTHER PUBLICATIONS

International Search Report for PCT/US2005/038519, completed on Feb. 22, 2006.
(Continued)

*Primary Examiner* — Kathleen Sonnett
*Assistant Examiner* — Jocelin Tanner
(74) *Attorney, Agent, or Firm* — Stoel Rives LLP

(57) ABSTRACT

A removable stent for placement within a lumen is provided. The stent includes a scaffolding of struts configured to define a substantially cylindrical member having a proximal end and a distal end. The stent also includes at least one flexible element spirally wound along at least a portion of a respective strut, wherein the element comprises at least one engageable member such that a force applied to the engageable member does not result in purse-stringing.

11 Claims, 2 Drawing Sheets

U.S. PATENT DOCUMENTS

| | | |
|---|---|---|
| 6,679,893 B1 | 1/2004 | Tran |
| 6,699,277 B1 | 3/2004 | Freidberg et al. |
| 6,802,846 B2 | 10/2004 | Hauschild et al. |
| 6,821,291 B2 | 11/2004 | Bolea et al. |
| 7,175,652 B2 | 2/2007 | Cook et al. |
| 7,252,680 B2 | 8/2007 | Freitag |
| 2002/0040236 A1 | 4/2002 | Lau et al. |
| 2002/0058986 A1 | 5/2002 | Landau et al. |
| 2002/0143387 A1* | 10/2002 | Soetikno et al. ............. 623/1.15 |
| 2002/0188344 A1* | 12/2002 | Bolea et al. ................. 623/1.11 |
| 2003/0149475 A1 | 8/2003 | Hyodoh et al. |
| 2004/0116996 A1* | 6/2004 | Freitag ......................... 623/1.11 |
| 2007/0233230 A1* | 10/2007 | Nissl et al. ................... 623/1.15 |
| 2007/0276463 A1 | 11/2007 | Nissl et al. |
| 2008/0033528 A1 | 2/2008 | Satasiya et al. |
| 2008/0140181 A1 | 6/2008 | Reynolds et al. |

FOREIGN PATENT DOCUMENTS

| | | |
|---|---|---|
| DE | 10335948 | 2/2005 |
| EP | 0 701 800 A1 | 3/1996 |
| EP | 0857471 | 8/1998 |
| EP | 1308138 A2 | 5/2003 |
| JP | 11-057022 | 3/1999 |
| WO | WO 00/44308 | 8/2000 |
| WO | WO 02/083037 | 10/2002 |
| WO | WO 03/022181 | 3/2003 |
| WO | WO 03/096935 A1 | 11/2003 |
| WO | WO 2005/079705 A1 | 9/2005 |

OTHER PUBLICATIONS

Advisory Action issued in U.S. Appl. No. 11/496,910 dated Nov. 18, 2009.
Examination Report for EP 04789198 dated Oct. 25, 2007.
International Search Report for PCT/US2004/031886 dated Feb. 7, 2005.
Office Action issued in U.S. Appl. No. 10/573,948 dated Nov. 5, 2009.
Office Action issued in U.S. Appl. No. 11/496,910 dated Oct. 15, 2009.
Office Action issued in U.S. Appl. No. 11/496,910 dated Mar. 18, 2009.
Restriction Requirement issued in U.S. Appl. No. 11/496,910 dated Feb. 3, 2009.
Supplementary European Search Report for EP 04789198 dated Apr. 5, 2007.
Office action dated Jun. 10, 2010 for U.S. Appl. No. 11/496,910.
Office Action dated May 5, 2011 for U.S. Appl. No. 11/496,910.
Office Action dated Jun. 24, 2010 for U.S. Appl. No. 10/573,948.
Office Action dated Dec. 14, 2010 for U.S. Appl. No. 11/496,910.
Notice of Allowance dated Feb. 16, 2011 for U.S. Appl. No. 10/573,948.

* cited by examiner

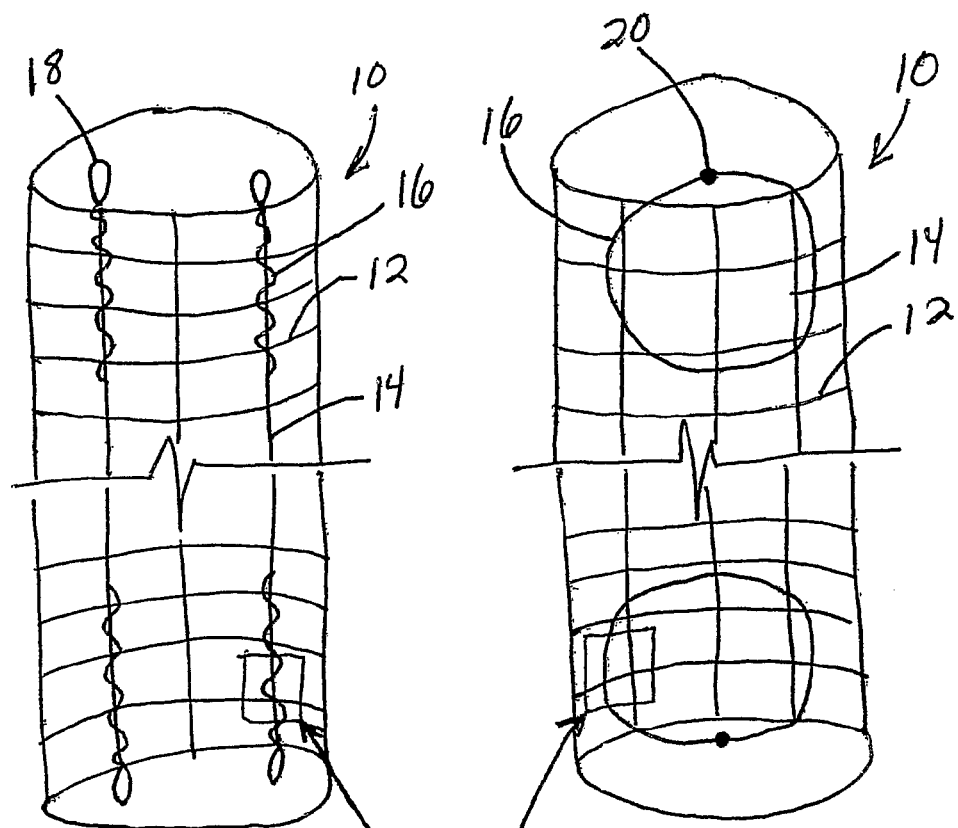
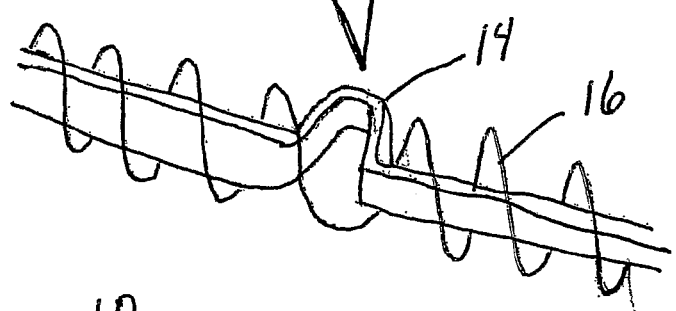
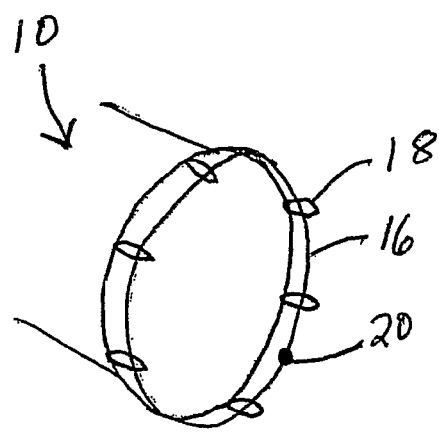

STENT REMOVAL AND REPOSITIONING AID AND ASSOCIATED METHOD

BACKGROUND OF THE INVENTION

1) Field of the Invention

The present invention relates to stents, in particular, to a stent removal and repositioning aid that promotes removal or repositioning a stent within a lumen.

2) Description of Related Art

Stents are devices that are inserted into body lumens such as vessels or passages to keep the lumen open and prevent closure due to a stricture, external compression, or internal obstruction. In particular, stents are commonly used to keep blood vessels open in the coronary arteries and they are frequently inserted into the ureters to maintain drainage from the kidneys, the bile duct for pancreatic cancer or cholangiocarcinoma, or the airways and esophagus for strictures or cancer. Vascular as well as nonvascular stenting has evolved significantly; unfortunately there remain significant limitations with respect to the technology for positioning and removing stents following implantation into various portions of a patient's anatomy.

In various areas of application, e.g., bronchus, biliary, trachea, or esophagus, the stents must be removable from the body or repositionable as a function of the course of the disease or treatment. This can be problematic since newly formed tissue can grow on the support frame of the stent and even grow through it, which can result in complications when removing a stent. In this regard, stents have been developed that include a support frame surrounded on the outside by a thread or wire. The support frame can be radially constricted by pulling on the thread ends that are each provided with a loop or the like, reducing a length of the thread engaged around the stent and creating a "purse-string" effect, which makes it possible for the frame to be removed or repositioned. However, when the wire or thread is guided or braided in multiple windings around the support frame, a high degree of friction results between the two stent components, which has a disadvantageous effect on the explantation process. In addition, stents having eyelets for looping the thread therethrough may have sharp edges that cause the thread to tear or break during the removal process.

Alternatively, physicians have grasped the thread ends with forceps or a similar instrument to reposition or remove the stent from within the lumen. However, this can be complex at times when the tissue has grown over the suture thread. Also, the suture may not be strong enough to remove the stent. Grasping may lead to damage to the stent itself, as the forceps may have difficulty accessing or adequately gripping the thread to remove or reposition the stent. Physicians may also use grasping forceps to grab the struts of the stent at a proximal end and remove the stent from the deployment site, but this also risks damage to the lumen or the stent, as the proximal end of the stent may be difficult to access.

Thus, there is a need in the industry for a stent that reduces the risk of damage to the stent, thread or suture, and/or the surrounding tissue during removal or repositioning of the stent. In addition, there is a need for a stent that provides for greater accessibility, as well as promotes effective repositioning and/or removal of the stent from a lumen.

BRIEF DESCRIPTION OF THE SEVERAL VIEWS OF THE DRAWINGS

Figure 1:
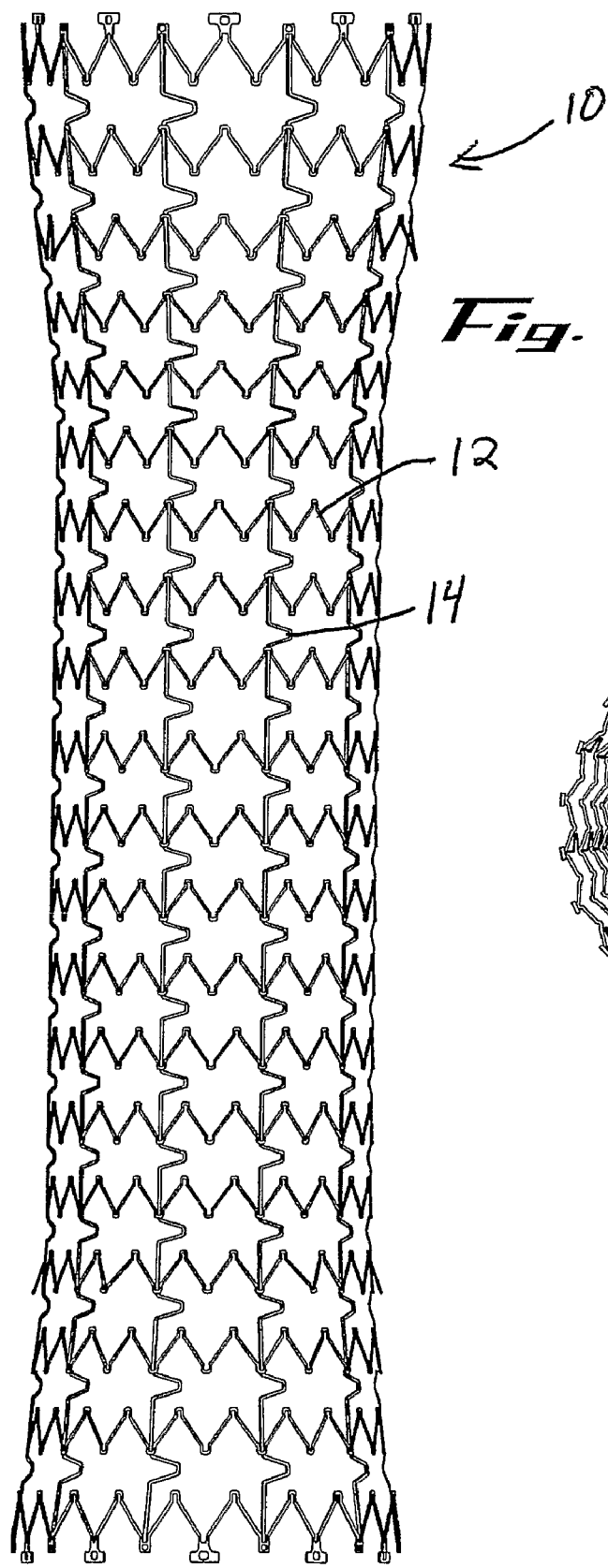
Figure 2:
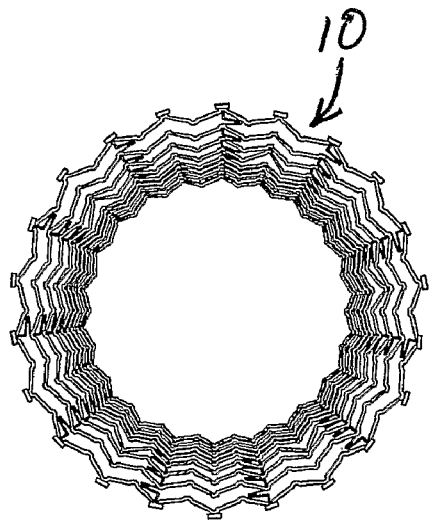

Having thus described the invention in general terms, reference will now be made to the accompanying drawings, which are not necessarily drawn to scale, and wherein:

FIG. 1 is a plan view of a stent having an interstice geometry, according to one embodiment of the present invention;

FIG. 2 is an end view of the stent shown in FIG. 1;

FIG. 3 is a perspective view of a stent including a plurality of sutures and illustrating each suture arranged throughout interstices of the stent, according to one embodiment of the present invention;

FIG. 4 is a perspective view of a stent including at least one suture and illustrating the suture arranged throughout interstices of the stent, according to another embodiment of the present invention;

FIG. 5 an enlarged perspective view of a suture arranged along the interstices of the stent shown in FIGS. 3-4, according to one embodiment of the present invention; and FIG. 6 is a partial perspective view of a stent including a plurality of suture loops and a suture extending therethrough, according to yet another embodiment of the present invention.

DETAILED DESCRIPTION OF THE INVENTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

With reference to FIGS. 1-2, a stent 10 is shown having interstice geometry. The stent 10 includes a scaffolding of struts. The struts generally include a plurality of interconnected legs 12 and connectors 14. As shown in FIG. 1, the stent 10 includes a series of legs 12 arranged circumferentially about the stent, as well as arranged in rows along the longitudinal axis of the stent, while a plurality of connectors 14 are arranged parallel to the longitudinal axis of the stent to connect the rows together. The stent 10 is formed of a memory metal that facilitates flexibility of the stent 10 such that the stent may be deformed and return to its original shape. As such, the legs 12 and connectors 14 of the stent 10 are preferably formed from a composite material such as Ni, C, Co, Cu, Cr, H, Fe, Nb, O, Ti and combinations thereof (e.g., Nitinol). The composite material is generally formed into a compressed tube from which the stent is etched and is formed on a suitable shaping device to give the stent the desired external geometry.

The stent 10 is generally cylindrical, having openings at the proximal and distal ends. As illustrated in FIG. 1, the diameter of the proximal and distal ends is slightly larger than the diameter of longitudinal portion of the stent extending therebetween. In the event the stent is to be shaped to the dimensions of a particular lumen, optical photography and/or optical videography of the target lumen may be conducted prior to stent formation. The interstice geometry of the stent then can be etched and formed in accordance with the requirements of that target lumen. For example, if the stent 10 were designed for the trachea, which has a substantially D shaped lumen and additionally the middle portion of the stent is preferably softer than the proximal or distal ends, the stent could be designed to those specifications. In particular, if the topography of the trachea of a particular patient is captured optically and the appropriate dimension provided, a patient specific prosthesis could be engineered. These techniques can be adapted to other non-vascular lumina but is very well suited for vascular applications where patient specific topography is a function of a variety of factors such as genetics, lifestyle, etc.

It should be pointed out that, unlike the use of differing shape memory materials to change regions of a stent 10, stents in accordance with the present invention can take on an infinite number of characteristic combinations of interstice geometry by changing angles, segment lengths, and segment thicknesses during the etching and forming stages of stent engineering or during post formation processing and polishing steps. Moreover, by modifying the geometry of the connectors 14, additional functionality may be achieved.

The stent could also include a cover, typically a polymer such as polyurethanes (e.g., polycarbonate urethane, or Chronoflex® manufactured by Cardiotech International), that is applied between the legs 12 and connectors 14 to provide a predetermined shape for the stent 10, as well as graft each of the legs and connectors into a unitary structure. The cover does not inhibit flexing or radial expansion of the stent 10, although it is possible to design the cover so that it controls the physical properties of the stent.

The suture 16 may be any suitable suture material, as known to those skilled in the art, such as polypropylene. However, it is understood that the term "suture" as used herein could be any suitable thread or wire or other material having a preferably flexible, but possibly inflexible, elongate shape, as known to those skilled in the art, capable of transferring force from forceps or a similar instrument to the stent 10 in alternative embodiments of the present invention.

Therefore, it is understood that any number of configurations of stents 10 could be incorporated and still be within the present scope of the invention. An exemplary embodiment of the interstice geometry of a stent 10 is disclosed in U.S. Patent Publication No. 20040127973 (application Ser. No. 10/674,972), entitled "Removable Biliary Stent," which is assigned to the present assignee and is incorporated herein by reference. Thus, the interstice geometry of the stent 10 should not be limited to that depicted in the disclosed Figures, as any number of configurations of interstice geometry could be employed with the present invention to achieve various degrees of rigidity and functionality. U.S. Patent Publication No. 20040122511 (application Ser. No. 10/669,450) entitled "Coated Stent with Geometry Determined Functionality and Method of Making the Same," which is assigned to the present assignee, is also incorporated herein by reference, and further describes a cover that may be employed with the present invention, including the types of materials and properties suitable for the cover, as well as the process of manufacturing the stent 10.

FIG. 3 illustrates a suture 16 intertwined about the legs 12 and connectors 14 of the stent 10. The suture 16 preferably defines a plurality of loops 18 located proximate to, and circumferentially about, at least one opening of the stent 10. However, in alternative embodiments there may be strands of suture 16 extending from the proximal and distal ends instead of loops 18 and, for example, the free end of the suture could have a knot that allows forceps or a similar instrument to grasp the end of the suture. The suture 16 typically extends along the longitudinal axis of the stent 10 from the proximal and/or distal end of the stent and stops three to four leg 12 segments along the connectors 14. However, the suture 16 could extend along the entire longitudinal axis of the stent 10 from the proximal to distal end or could extend any number or leg 12 segments along a respective connector 14. Each loop 18 is sized and configured to receive forceps or a similar instrument, and at least a portion of the remaining suture 16 opposite that of the loop is attached to the legs 12 and/or connectors 14 to prevent the suture from coming loose or completely disengaged from the stent 10. Each loop 18 is attached to the stent 10 such that a force applied through the suture 16 transfers force through the loops and to the stent. The suture 16 could include, for example, a knot that secures the suture to the stent, but an adhesive, a fastener, or similar technique could also be used that is capable of effectively transferring force. In addition, the suture 16 could also be held in place on the stent 10 by a cover and struts on a covered stent. For instance, the suture 16 could be formed integral with the cover and struts of the stent 10 such that knots and the like would not be required.

Therefore, when forceps or a similar instrument pulls on one or more of the loops 18 at the proximal end of the stent 10, the stent is urged in the direction of pulling such that the stent may be repositioned within a lumen or completely removed. Moreover, the forceps could also be positioned through the axis of the stent 10 and through one or more loops to push the stent at the distal end of the stent, such that the stent is pushed to a different position or removed from the lumen. In this regard, pulling or pushing on the loops 18 does not create a purse-string effect and consequently, the expanded diameter of the stent 10 is unlikely to change during repositioning or explantation. Eliminating the purse-string effect reduces the risk of re-expansion failure, such as by plastic deformation of the stent, when the stent 10 is repositioned within the lumen.

FIG. 4 illustrates an alternative embodiment, wherein the suture 16 is arranged in a single loop, with the ends of the loop connected with a knot 20. The loop extends from the proximal and/or distal end of the stent 10, along one or more connectors 14, along a series of legs 12, and along one or more additional connectors. The loop could be arranged about any number of legs 12 and connectors 14, and even along the entire longitudinal axis from the proximal to the distal end of the stent. In addition, there could be any number of loops about the circumference of the stent in alternative embodiments. The loop of suture 16 is typically intertwined about at least a portion of the legs 12 and connectors 14 and secured with a knot or similar fastening technique such that application of a force on the suture transfers the force to the stent 10. However, as described above, the suture 16 could also be held in place on the stent 10 by a cover and struts on a covered stent. For instance, the suture 16 could be formed integral with the cover and struts of the stent 10 such that knots and the like would not be required. As before with respect to FIG. 3, in alternative embodiments there may be strands of suture 16 extending from the proximal and distal ends instead of forming a loop 18 and, for example, the free ends of the suture could each have a knot that allows forceps or a similar instrument to grasp one or both ends of the suture.

Like the stent 10 shown in FIG. 3, the stent depicted in FIG. 4 also does not create a purse-string effect. Thus, when forceps or a similar instrument pulls on one or more of the loops 16 at the proximal end of the stent 10, the stent is also pulled such that the stent may be repositioned within the lumen or completely removed without changing the expanded diameter of the stent. Similarly, the forceps could be positioned through the longitudinal axis of the stent 10 to engage a loop of suture 16 at the distal end of the stent to push the stent to a different position or to remove the stent from the lumen.

FIG. 5 illustrates that the suture 16 is preferably arranged about the connectors 14 in a spiral-like configuration. Arranging the suture 16 in a spiral-like configuration distributes the force along each connector 14 when forceps or a similar instrument pulls upwardly or pushes downwardly on each loop 18 shown in FIGS. 3 and 4. Therefore, the spiral-like configuration reduces the risk that the suture 16 will break or become dislodged during repositioning or removal of the stent 10. It is understood that the suture 16 could be arranged about the legs 12 and/or connectors 14 in the configuration shown in FIG. 5, but is not required to have this particular configuration, as there may be alternative configurations in additional embodiments. In addition, the suture 16 in FIG. 5 is shown as being loosely arranged about the connector 14 for illustrative purposes only, as the suture will typically be in more intimate contact with the scaffolding of the stent 10 or tightly wound about the connector.

In an additional embodiment of the present invention, FIG. 6 depicts a stent 10 having a series of loops 18 arranged about the circumference of the stent at the proximal and/or distal end. The loops 18 are preferably a suture material, and there may be any number of loops about the circumference of the stent 10. The stent 10 also includes a loop of suture 16 that extends about the circumference of the loop, through the loops 18, and connects to itself with a knot 20. The loops 18 could be connected to the stent 10 in the manner described above in conjunction with FIGS. 3-5, or the loops could be attached to the outer periphery of the proximal and/or distal end of the stent. Furthermore, the loops 18 could be a single piece of suture circumferentially disposed about the proximal and/or distal end of the stent 10, or one or more loops could be a single suture. The loops 18 are attached to the stent 10 such that a force applied through the suture 16 transfers force through the loops and to the stent.

Unlike the embodiments shown in FIGS. 3 and 4, the stent 10 shown in FIG. 6 creates a purse string effect. As such, pulling or pushing on the suture 16 with forceps or a similar instrument causes the proximal and/or distal end of the stent 10 to purse string. Thus, forceps or a similar instrument could be used to purse string the proximal end of the stent 10 by pulling on the suture 16, while pushing on the suture at the distal end of the stent will cause the distal end to purse string. Purse stringing the suture 16 crimps the proximal or distal end of the stent 10 to promote repositioning or removal of the stent from the lumen. Once the suture 16 is released, the proximal or distal end of the stent 10 will expand.

The present invention provides several advantages. Providing one or more loops from a suture material allows forceps or a similar instrument to engage the loops rather than the stent 10 itself. Therefore, the embodiments of the present invention facilitate easier removal or repositioning of the stent 10 without increasing the likelihood of damage to the stent and/or the lumen. Furthermore, the suture is arranged about the stent 10 to distribute the forces applied during repositioning or removal of the stent, which reduces the risk that the suture and/or stent will be damaged or dislodged.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A removable stent for placement within a lumen comprising:
    a scaffolding of struts including a plurality of legs and one or more connectors, the plurality of legs arranged in rows about a circumference of the stent, the rows arranged longitudinally along a longitudinal axis of the stent and connected by the one or more connectors, the scaffolding of struts formed of metal and configured to define a substantially cylindrical member having a proximal end and a distal end; and
    a plurality of flexible engageable members arranged circumferentially about an outer periphery of at least one of the proximal and distal ends, wherein the engageable members comprise a suture formed of a material different from the metal of the scaffolding, are distinct from the scaffolding, and are directly attached to the scaffolding in a manner that a force applied to the engageable members transfers directly to the scaffolding, wherein each of the engageable members extends proximally from the proximal end or distally from the distal end, and wherein each of the engageable members comprises a spiral completely and longitudinally around a connector of the scaffolding of struts; and
    at least one element disposed within each of the engageable members and about the circumference of the proximal or distal end and connected to itself, wherein the at least one element comprises a suture, and wherein a force applied to the element at the proximal or distal end causes the proximal or distal end to reduce in diameter.

2. The stent according to claim 1, wherein the suture of the plurality of engageable members comprises thread.

3. The stent according to claim 1, wherein the plurality of engageable members comprise loops.

4. The stent according to claim 1, wherein the at least one element comprises a different material than the scaffolding.

5. A method for removing or repositioning a stent within a lumen, the stent comprising the removable stent of claim 1 the method comprising:
    engaging at least one element disposed within each of the engageable members and about the circumference of the proximal or distal end and connected to itself, wherein the at least one element comprises a suture; and
    applying a force to the element at the proximal or distal end such that the force transfers to the engageable members and the proximal or distal end reduces in diameter.

6. The method according to claim 5, wherein applying a force to the element comprises pulling the at least one element proximally at a proximal end of the stent.

7. The method according to claim 5, wherein applying a force to the element comprises pushing the at least one element distally at a distal end of the stent.

8. A removable stent for placement within a lumen comprising:
    a scaffolding of struts including legs and connectors formed of metal and configured to define a substantially cylindrical member having a proximal end and a distal end; and
    a plurality of engageable members that are distinct from the scaffolding, directly attached to the scaffolding in a manner that a force applied to the engageable members transfers directly to the scaffolding, and arranged circumferentially about an outer periphery of at least one of the proximal and distal ends, wherein each of the engageable members extends proximally from the proximal end or distally from the distal end, and wherein each of the engageable members comprises a spiral completely and longitudinally around a connector of the scaffolding of struts to attach to the scaffolding; and
    at least one element disposed within each of the engageable members and about the circumference of the proximal or distal end and connected to itself, wherein a force applied to the element at the proximal or distal end causes the proximal or distal end to reduce in diameter, and wherein the plurality of engageable members each comprise a flexible suture comprising one of thread or polypropylene, and the at least one element comprises a flexible suture.

9. The stent according to claim 8, wherein the at least one element comprises a different material than the scaffolding.

10. The stent according to claim 8, wherein the flexible suture of the at least one element, comprises thread.

11. The stent according to claim 8, wherein the plurality of engageable members are independent of the scaffolding and attached thereto.

* * * * *